US00PP19367P2

(12) United States Plant Patent
Trucks

(10) Patent No.: US PP19,367 P2
(45) Date of Patent: Oct. 21, 2008

(54) ***PANICUM* PLANT NAMED 'PRAIRIE FIRE'**

(50) Latin Name: *Panicum virgatum*
Varietal Denomination: Prairie Fire

(76) Inventor: Gary M. Trucks, 1460 Hillandale Rd., Benton Harbor, MI (US) 49022-9761

( * ) Notice: Subject to any disclaimer, the term of this patent is extended or adjusted under 35 U.S.C. 154(b) by 0 days.

(21) Appl. No.: 11/881,884

(22) Filed: Jul. 30, 2007

(51) Int. Cl.
*A01H 5/00* (2006.01)

(52) U.S. Cl. ..... Plt./384

(58) Field of Classification Search ..... Plt./384
See application file for complete search history.

*Primary Examiner*—Kent L. Bell
*Assistant Examiner*—June Hwu

(57) ABSTRACT

A new and distinct cultivar of ornamental *Panicum virgatum* plant named 'Prairie Fire' with erect culms and becoming deep wine red early in the season, suitable as a potted plant, for mass or specimen landscaping, and for cut flower arrangements.

2 Drawing Sheets

Botanical classification: *Panicum virgatum.*
Variety denomination: 'Prairie Fire'.

SUMMARY, BACKGROUND AND ORIGIN OF THE PLANT

*Panicum virgatum* 'Prairie Fire', hereinafter also referred to as 'Prairie Fire' and "the plant" is a new and distinct cultivar of Switch Grass. It was cross by Gary M. Trucks in 2001 between *Panicum* 'Heavy Metal' (not patented)× *Panicum* 'Rostrahlbush' (not patented) at a nursery in Benton Harbor, Mich. and selected for further observation in 2002. The new plant has been asexually reproduced by division at the same perennial plant nursery in Benton Harbor, Mich. and found to produce identical plants that maintain the unique characteristics of the original plant. The plant is stable and reproduces true to type in successive generations of asexual reproduction.

'Prairie Fire' differs from its parents as well as all other *Panicum* known to the applicant, in that the plant develops a dark wine colored foliage early, grows taller and more prolifically and produces erect flowers. The most similar known Switch Grass cultivars are 'Shenandoah' (not patented) and 'RR1' U.S. Plant Pat. No. 17,944. Both cultivars develop purplish foliage with 'Shenandoah' more arching foliage and coloring later, and 'RR1' being much shorter than 'Prairie Fire'. *Panicum* 'Rostrahlbush' develops a more reddish purplish color later in the season and is shorter than 'Prairie Fire'. 'Heavy Metal', the other parent, is much more blue green and does not develop any purplish foliage color.

TABLE 1

| CULTIVAR | HEIGHT (cm) | INITIAL COLOR | SEASONAL COLOR | SEASON OF CHANGE | HABIT |
|---|---|---|---|---|---|
| 'Prairie Fire' | 100 | Blue green | Grayed purple | Early July | Upright |
| 'Haense Herms' | 100 | Green | Red purple | Early August | Upright |
| 'Heavy Metal' | 130 | Blue green | Blue green | None | Upright |

TABLE 1-continued

| CULTIVAR | HEIGHT (cm) | INITIAL COLOR | SEASONAL COLOR | SEASON OF CHANGE | HABIT |
|---|---|---|---|---|---|
| 'Rostrahlbush' | 110 | Green | Red purple | Early August | Upright |
| RR1 | 55 | Blue green | Red purple | Mid July | Upright |
| 'Shenandoah' | 140 | Blue green | Red purple | Late July | arching |

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

GENERAL DESCRIPTION OF THE PLANT

Figure 1:
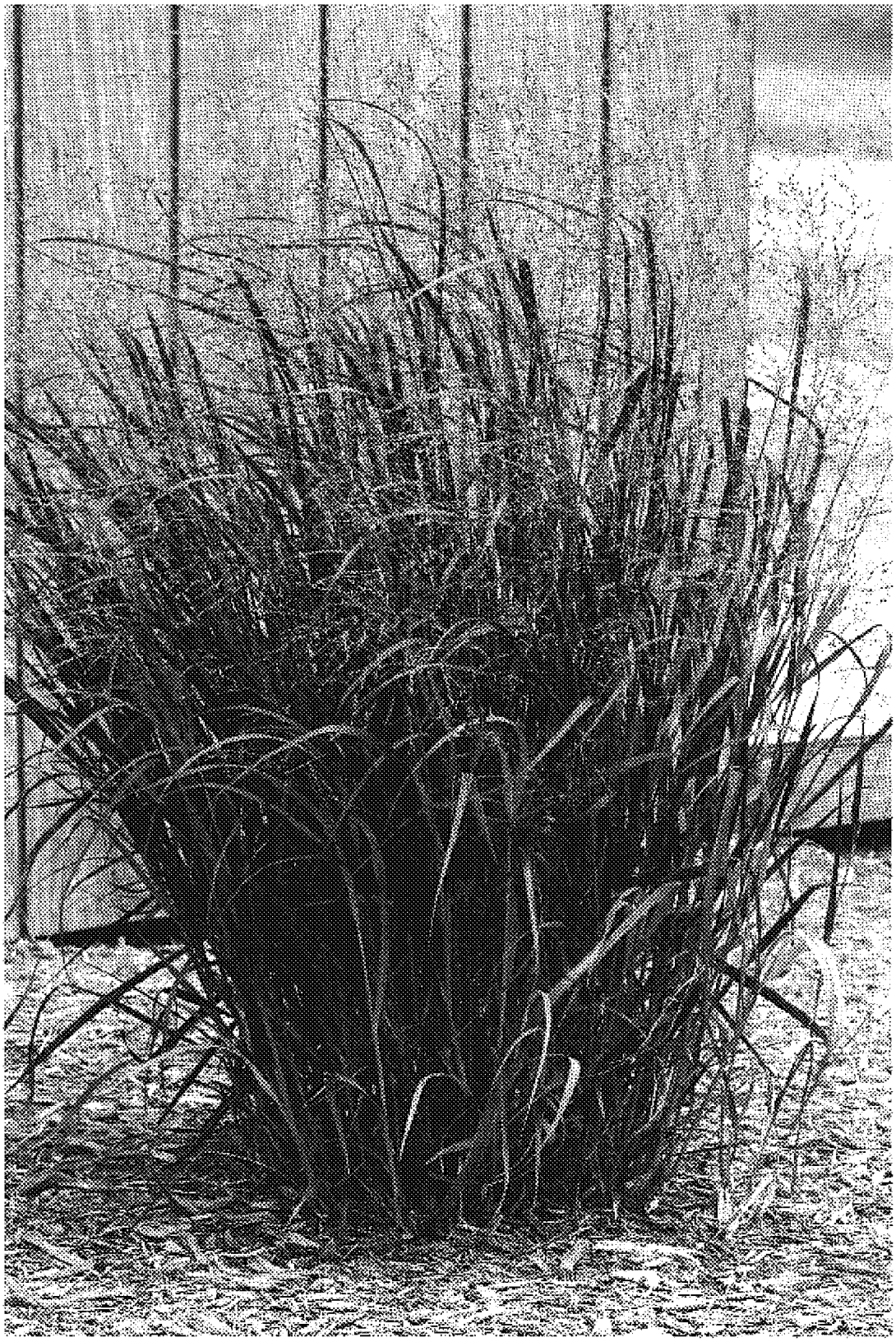
FIG. 1 shows the overall plant in mid-season.
Figure 2:
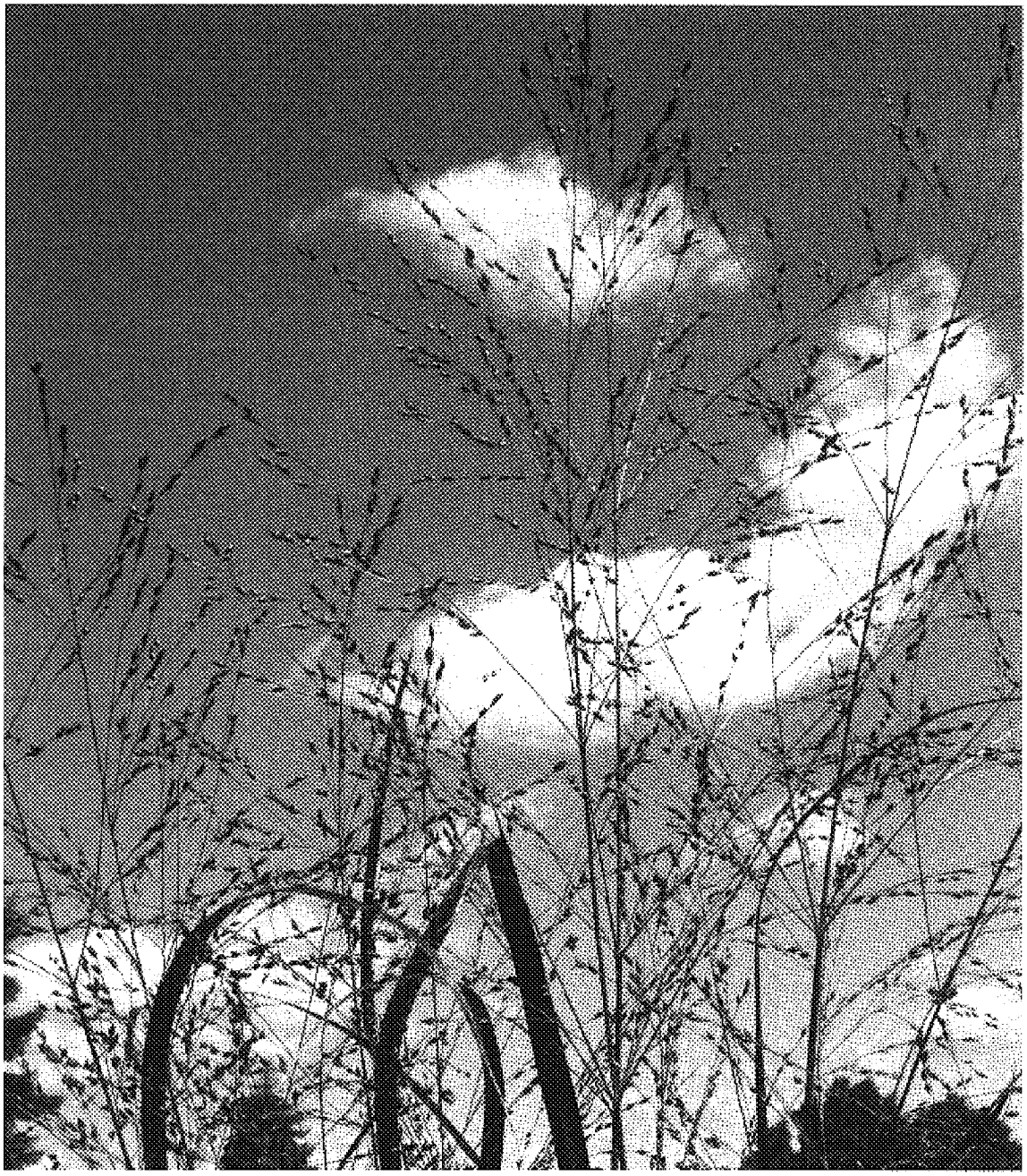
FIG. 2 shows the inflorescence in mid-July.

*Panicum virgatum* is native to all but the Pacific Coast states of the Mainland United States in addition to parts of Canada and Central America. There are several selected cultivars in production or commerce. *Panicum virgatum* 'Prairie Fire' differs from all of these known to the inventor in that it has:

1. Blue green foliage that develops early in the season to a deep grayed purple.
2. Upright and less arching habit.

DETAILED BOTANICAL DESCRIPTION

The following descriptions and color references are based on the 2001 edition of The Royal Horticultural Society Colour Chart except where common dictionary terms are used. The new plant, 'Prairie Fire', has not been observed under all possible environments. The phenotype may vary slightly with different environmental conditions, such as temperature, light, fertility, moisture and maturity levels, but without any change in the genotype. The following observations and size descriptions are of a three-year old plant in a trail garden in Zeeland, Mich. in full sun with supplemental water and fertilizer.

Parentage: Controlled cross of *Panicum virgatum. Panicum* 'Heavy Metal'×*Panicum virgatum* 'Rostrahlbush'.

Propagation:

*Method.*—By division of the culms.

*Time to finishing in a 65 cm pot.*—Three months.

*Rooting habit.*—Normal, coarsely branching.

Plant description:

*Plant shape and habit.*—Hardy herbaceous perennial forming tightly rhizomatous clump, with upright culms topped with finely textured airy inflorescence.

*Plant size.*—Foliage height at flowering is 96 to 102 cm tall from soil line to the top of the leaves and 45 to 50 cm wide at soil line and 80 to 85 cm at widest point just below flowers;

Foliage description: Glabrous, entire, flat, alternate, erect to arching toward tips, sheathed from node of attachment to ligule, linear, deciduous but persist through winter;

*Foliage size.*—40 to 48 cm long, averaging 46 cm; 9 to 12 mm wide, averaging 11 mm. Top surface early season: RHS 137C. Underside center early season: closest to RHS 138B.

Top surface mid season and later: RHS 187A.

Underside center mid season and later: RHS 1887B;

Veins: parallel; color same as the surrounding leaf on both the top and bottom of the leaf.

*Culm* (*stem*).—Erect, cylindrical, completely enclosed by leaf sheath, 120 to 130 cm long including panicle and 3.0 to 4.0 mm wide; internode length 16 to 18 cm; RHS 187A near nodes and where receiving full sun exposure, RHS 137B with a slight glaucous bloom.

*Flower description.*—Finely branched open panicle, one per culm, persists through winter; No fragrance detected.

Panicle: Pyramidal, 35 to 40 cm long, 30 to 32 cm wide; RHS 138B;

Glumes: Lowest outside — 3 mm long and 2 mm wide RHS 59A, inside 4 to 5.0 mm long.

Spikelet: 5.0 to 6.0 mm long and 2.5 mm wide.

*Gynoecium.*—Stigma: two, feathered, protruding 1 to 2 mm from glume, RHS 59A.

*Androecium.*—Filaments — fine, hair-like, while less than 1 mm diameter and up to 2.0 mm long; Anthers — 2.0 to 3.0 mm long, 1.0 mm wide, closest to RHS 31A.

*Pollen.*—Elliptical, less than 0.1 mm long, nearest RHS N 25C.

*Fruit.*—Caryopsis; 2 to 3 mm long and 1.5 mm wide, nearest RHS 164C.

Hardiness, pest and disease resistance: The plant grows best with plenty of moisture and adequate drainage, but is able to tolerate some drought when mature. Hardiness at least from USDA zone 4 through 9. Disease and pest resistance beyond what is typical of that of other Switch Grasses has not been observed.

What is claimed is:

1. A new and distinct cultivar of ornamental *Panicum virgatum* Plant named 'Prairie Fire' as herein described and illustrated, with erect culms and becoming deep wine red early in the season, suitable as a potted plant, for the garden, and for cut flower arrangements.

* * * * *